(12) United States Patent
Trommeter et al.

(10) Patent No.: US 9,808,252 B2
(45) Date of Patent: Nov. 7, 2017

(54) VASCULAR OCCLUSION DEVICES

(75) Inventors: Julie Marie Trommeter, Lafayette, CO (US); Michael B. Lyons, Boulder, CO (US); Jeffrey Paul Castleberry, Longmont, CO (US); Robin Shandas, Boulder, CO (US); James Fogelberg, Boulder, CO (US); Stephen Johnson, Golden, CO (US)

(73) Assignees: ENDOSHAPE, INC., Boulder, CO (US); THE REGENTS OF THE UNIVERSITY OF COLORADO, A BODY CORPORATE, Denver, CO (US)

( * ) Notice: Subject to any disclaimer, the term of this patent is extended or adjusted under 35 U.S.C. 154(b) by 2 days.

(21) Appl. No.: 13/262,546

(22) PCT Filed: Apr. 2, 2010

(86) PCT No.: PCT/US2010/029742
§ 371 (c)(1),
(2), (4) Date: Sep. 30, 2011

(87) PCT Pub. No.: WO2010/115076
PCT Pub. Date: Oct. 7, 2010

(65) Prior Publication Data
US 2012/0046687 A1 Feb. 23, 2012

Related U.S. Application Data

(60) Provisional application No. 61/166,120, filed on Apr. 2, 2009.

(51) Int. Cl.
*A61M 29/00* (2006.01)
*A61B 17/12* (2006.01)
(Continued)

(52) U.S. Cl.
CPC .... *A61B 17/12022* (2013.01); *A61B 17/1215* (2013.01); *A61B 17/12109* (2013.01);
(Continued)

(58) Field of Classification Search
CPC ........ A61B 17/12022; A61B 17/12145; A61B 17/1215; A61B 17/12109;
(Continued)

(56) References Cited

U.S. PATENT DOCUMENTS 3,490,456 A * 1/1970 Kortum .................... A61F 6/144
128/839
4,503,569 A * 3/1985 Dotter ......................... 623/1.19
(Continued)

FOREIGN PATENT DOCUMENTS

CA 2527976 A1 12/2004
EP 2098174 A2 9/2009
(Continued)

OTHER PUBLICATIONS

Extended European Search Report and Opinion dated Dec. 8, 2014, EP Application No. 10842570.3, 6 pages.
(Continued)

*Primary Examiner* — Richard Louis
(74) *Attorney, Agent, or Firm* — Dorsey & Whitney LLP

(57) ABSTRACT

Shape memory materials (SMM) are formed as coil-shaped vascular occlusion devices upon deployment. Shape memory polymer (SMP) materials are tailored through formulation for specific mechanical behavior of the coils. Concurrent coil diameter changes enhance the relative change in stiffness along the length of the coil. Interconnecting structures (104*a/b*) are formed on ends of elongated members (102*a*) in the pre-deployment shape for multiple coil insertion capability within an introducer. Channels (206) are formed in pre-deployment shape, elongate mem-
(Continued)

bers (202) that allow access for injection of imaging contrast agent or concurrent placement of instruments. A single SMM occlusive device (300) transforms into multiple, smaller diameter coils (302b) in the deployed state to generate a complex occlusive structure. A SMM occlusive device (400) has a collapsed fabric (404) component attached to and extending along a sidewall during storage and insertion, and then deploys as a coil (402b) to form a single- or multiple-layer occlusive fabric surface within a center of the coil (402b).

15 Claims, 5 Drawing Sheets

(51) Int. Cl.
  *A61L 31/04* (2006.01)
  *A61L 31/14* (2006.01)
  *A61B 17/00* (2006.01)
(52) U.S. Cl.
  CPC ........ *A61B 17/12145* (2013.01); *A61L 31/04* (2013.01); *A61L 31/14* (2013.01); *A61B 17/12113* (2013.01); *A61B 2017/00477* (2013.01); *A61B 2017/00778* (2013.01); *A61B 2017/00871* (2013.01); *A61B 2017/00898* (2013.01); *A61B 2017/12054* (2013.01); *A61L 2400/16* (2013.01); *A61L 2430/36* (2013.01)
(58) Field of Classification Search
  CPC  A61B 2017/00778; A61B 2017/00898; A61B 2017/12054; A61B 17/12113; A61B 2017/00477; A61L 31/04; A61L 31/14; A61L 2430/36
  USPC .......................................... 606/200, 191, 108
  See application file for complete search history.

(56) References Cited

U.S. PATENT DOCUMENTS

| | | | |
|---|---|---|---|
| 4,606,336 A | 8/1986 | Zeluff | |
| 4,950,258 A | 8/1990 | Kawai et al. | |
| 4,994,069 A | 2/1991 | Ritchart et al. | |
| 5,163,952 A | 11/1992 | Froix | |
| 5,258,020 A | 11/1993 | Froix | |
| 5,383,204 A * | 1/1995 | Gibbs et al. | 714/758 |
| 5,599,291 A | 2/1997 | Balbierz et al. | |
| 5,603,722 A | 2/1997 | Phan et al. | |
| 5,649,949 A | 7/1997 | Wallace et al. | |
| 5,669,931 A * | 9/1997 | Kupiecki et al. | 606/191 |
| 5,674,242 A | 10/1997 | Phan et al. | |
| 5,800,455 A * | 9/1998 | Palermo et al. | 606/191 |
| 5,830,230 A * | 11/1998 | Berryman et al. | 606/200 |
| 5,941,888 A * | 8/1999 | Wallace et al. | 606/108 |
| 5,964,744 A | 10/1999 | Balbierz et al. | |
| 6,086,577 A * | 7/2000 | Ken et al. | 606/1 |
| 6,090,125 A | 7/2000 | Horton | |
| 6,160,084 A | 12/2000 | Langer et al. | |
| 6,165,198 A | 12/2000 | McGurk et al. | |
| 6,221,066 B1 | 4/2001 | Ferrera et al. | |
| 6,248,129 B1 | 6/2001 | Froix | |
| 6,281,262 B1 | 8/2001 | Shikinami | |
| 6,368,356 B1 | 4/2002 | Zhong et al. | |
| 6,383,204 B1 * | 5/2002 | Ferrera et al. | 606/191 |
| 6,388,043 B1 | 5/2002 | Langer et al. | |
| 6,550,480 B2 | 4/2003 | Feldman et al. | |
| 6,551,305 B2 | 4/2003 | Ferrera et al. | |
| 6,554,849 B1 * | 4/2003 | Jones et al. | 606/200 |
| 6,616,617 B1 | 9/2003 | Ferrera et al. | |
| 6,712,810 B2 | 3/2004 | Harrington et al. | |
| 6,720,402 B2 | 4/2004 | Langer et al. | |
| 6,740,094 B2 | 5/2004 | Maitland et al. | |
| 6,746,461 B2 | 6/2004 | Fry | |
| 6,887,266 B2 | 5/2005 | Williams et al. | |
| 7,115,691 B2 | 10/2006 | Alvarado et al. | |
| 7,208,550 B2 | 4/2007 | Mather et al. | |
| 7,217,744 B2 | 5/2007 | Lendlein et al. | |
| 7,611,524 B1 | 11/2009 | Maitland et al. | |
| 2002/0016613 A1 * | 2/2002 | Kurz et al. | 606/213 |
| 2002/0052613 A1 | 5/2002 | Ferrera et al. | |
| 2002/0161397 A1 * | 10/2002 | Mathews et al. | 606/200 |
| 2002/0173839 A1 | 11/2002 | Leopold et al. | |
| 2003/0066533 A1 | 4/2003 | Loy | |
| 2003/0083735 A1 | 5/2003 | Denardo et al. | |
| 2003/0149470 A1 | 8/2003 | Alvarado et al. | |
| 2003/0153972 A1 * | 8/2003 | Helmus | 623/1.15 |
| 2003/0199919 A1 * | 10/2003 | Palmer et al. | 606/200 |
| 2004/0030062 A1 | 2/2004 | Mather | |
| 2004/0091543 A1 * | 5/2004 | Bell et al. | 424/489 |
| 2004/0122174 A1 | 6/2004 | Mather et al. | |
| 2004/0193246 A1 | 9/2004 | Ferrera | |
| 2005/0004598 A1 * | 1/2005 | White et al. | 606/200 |
| 2005/0021074 A1 | 1/2005 | Elliott | |
| 2005/0033163 A1 | 2/2005 | Duchon et al. | |
| 2005/0038460 A1 | 2/2005 | Jayaraman | |
| 2005/0171572 A1 | 8/2005 | Martinez | |
| 2005/0212630 A1 | 9/2005 | Buckley | |
| 2005/0234540 A1 | 10/2005 | Peavey et al. | |
| 2006/0006649 A1 * | 1/2006 | Galdonik | A61M 25/0905 285/417 |
| 2006/0030933 A1 | 2/2006 | DeLegge et al. | |
| 2006/0036045 A1 | 2/2006 | Wilson et al. | |
| 2006/0041089 A1 | 2/2006 | Mather et al. | |
| 2006/0079926 A1 | 4/2006 | Desai et al. | |
| 2006/0095134 A1 | 5/2006 | Trieu et al. | |
| 2006/0129232 A1 | 6/2006 | Dicarlo et al. | |
| 2006/0142794 A1 | 6/2006 | Lendlein et al. | |
| 2006/0155324 A1 * | 7/2006 | Porter | A61B 17/12022 606/200 |
| 2006/0206140 A1 | 9/2006 | Shaolian et al. | |
| 2006/0213522 A1 | 9/2006 | Menchaca et al. | |
| 2006/0241682 A1 * | 10/2006 | Kurz | 606/200 |
| 2006/0241686 A1 | 10/2006 | Ferrera et al. | |
| 2006/0280768 A1 | 12/2006 | Hwang et al. | |
| 2007/0016233 A1 | 1/2007 | Ferrera et al. | |
| 2007/0083226 A1 * | 4/2007 | Buiser | A61B 17/12022 606/200 |
| 2007/0141339 A1 | 6/2007 | Song et al. | |
| 2007/0142893 A1 | 6/2007 | Buiser et al. | |
| 2007/0233037 A1 | 10/2007 | Gifford, III et al. | |
| 2007/0239199 A1 | 10/2007 | Jayaraman | |
| 2008/0004692 A1 | 1/2008 | Henson | |
| 2008/0082176 A1 | 4/2008 | Slazas | |
| 2008/0097508 A1 | 4/2008 | Jones et al. | |
| 2008/0114391 A1 * | 5/2008 | Dieck et al. | 606/200 |
| 2008/0147111 A1 | 6/2008 | Johnson et al. | |
| 2008/0195139 A1 | 8/2008 | Donald et al. | |
| 2008/0215085 A1 * | 9/2008 | Whisenant | A61B 18/1492 606/213 |
| 2008/0281405 A1 | 11/2008 | Williams et al. | |
| 2008/0312733 A1 | 12/2008 | Jordan | |
| 2008/0319532 A1 | 12/2008 | Monstadt | |
| 2009/0056722 A1 | 3/2009 | Swann | |
| 2009/0099647 A1 | 4/2009 | Glimsdale et al. | |
| 2009/0112251 A1 | 4/2009 | Qian et al. | |
| 2009/0275974 A1 | 11/2009 | Marchand et al. | |
| 2010/0063582 A1 | 3/2010 | Rudakov | |
| 2011/0196487 A1 | 8/2011 | Badawi et al. | |
| 2013/0096427 A1 * | 4/2013 | Murray | A61N 5/1001 600/433 |

FOREIGN PATENT DOCUMENTS

| | | | |
|---|---|---|---|
| EP | 2098174 A3 | 9/2009 | |
| JP | 2001/520085 A | 10/2001 | |
| WO | 94/06503 A1 | 3/1994 | |
| WO | 0010469 A1 | 3/2000 | |
| WO | 00/62711 A1 | 10/2000 | |
| WO | 2004/110313 A1 | 12/2004 | |
| WO | 2008/051254 A1 | 5/2008 | |

(56) References Cited

FOREIGN PATENT DOCUMENTS

| WO | 2010/115076 A2 | 10/2010 |
|---|---|---|
| WO | 2010/135352 A1 | 11/2010 |
| WO | 2011/084536 A2 | 7/2011 |

OTHER PUBLICATIONS

Author Unknown, 0.18 and 0.035 Fibered Platinum Coils, Boston Scientific (www.bostonscientific.com), accessed Jan. 2010, pp. 1.

Author Unknown, Brain Aneurysm Treatment, Boston Scientific (www.bostonscientific.com), accessed Jan. 2010, pp. 2.

Author Unknown, Matrix2 Detachable Coils, Occlusion is only the beginning . . . , Boston Scientific (www.bostonscientific.com), accessed Jan. 2010, pp. 1-8.

Author Unknown, Neurovascular Intervention, Boston Scientific (www.bostonscientific.com), accessed Jan. 2010, pp. 2.

Author Unknown, Shape Memory Therapeutics Receives Texas Emerging Technology Fund Award, Biomedical Engineering, Texas A&M University, Oct. 21, 2009, pp. 2.

Author Unknown, VortX 18 and 35 Vascular Occlusion Coils, Boston Scientific (www.bostonscientific.com), accessed Jan. 2010, pp. 2.

Codman & Shurtleff, Inc., Trufill DCS Orbit Detachable Coil System, http://www.codman.com/DePuy/products/Products/neurovascular/trufillorbit/index.html, accessed Jan. 2010.

De Nardo, Luigi et al., Shape memory polymer foams for cerebral aneurysm reparation: Effects of plasma sterilization on physical properties and cytocompatibility, www.sciencedirect.com, ActaBioMaterialia, 2009, pp. 1508-1518.

EV3 Inc., Embolic Coils, ev3 Inc., http://www.ev3.net/neuro/intl/embolic-coils/nxt-detachable-coils5391.htm, accessed Jan. 2010, pp. 1.

Gall, Ken et al., Thermomechanics of the Shape Memory effect in polymers for biomedical applications, J. Biomed Mater Res 73A, 2005; 73(3): pp. 339-348, Apr. 1, 2005 (www.interscience.wiley.com) Wiley Int Science, (2005).

Hampikian, Janet M. et al., Mechanical and radiographic properties of a shape memory polymer composite for intracranial aneurysm coils, Materials Science and Engineering C 26, (2006), pp. 1373-1379.

Heaton, Brian C., A Shape Memory Polymer for Intracranial Aneurysm Coils: An Investigation of Mechanical and Radiographic Properties of a Tantalum-Filled Shape Memory Polymer Composite, Georgia Institute of Technology, Jul. 2004, pp. 1-60.

Maitland, D. J. et al., Photothermal properties of shape memory polymer micro-actuators for treating stroke, Las. Surg. Med., vol. 30, No. 1, 2002, pp. 1-11.

Maitland, Duncan J. et al., Design and Realization of Biomedical Devices Based on Shape Memory Polymers, Materials Research Society, Spring 2009.

Maitland, Duncan J. et al., "Prototype laser-activated shape memory polymer foam device for embolic treatment of aneurysms", Journal of Biomedical Optics, May/Jun. 2007, vol. 12(3), pp. 1-4.

Metzger, M. F. et al., Mechanical properties of mechanical actuator for treating ischemic stroke, Biomed. Microdevices, vol. 4, No. 2, 2002, Nov. 2, 2002, pp. 89-96.

Microvention Terumo, HydroSoft, http://www.microvention.com/Products/Coils/HydrogelProducts/HydroSoft/tabid/70/default.aspx, accessed Jun. 8, 2010, pp. 2.

Microvention Terumo, MicroPlex Coil System, http://www.microvention.com/Products/Coils/MicroPlexProducts/tabid/63/default.aspx, accessed Jun. 8, 2010, pp. 1.

Microvention Terumo, The Facts About HydroCoil, http://www.microvention.com/Products/Coils/HydrogelProducts/HydroCoil/tabid/69/Default.aspx, accessed Jun. 8, 2010, pp. 2, 1-2.

Micrus Endovascular, Enhanced Embolic Coils for the Treatment of Cerebral Aneurysms, http://www.micrusendovascular.com/products/cerebyte_intl.asp?ln=h, accessed Jan. 2010, pp. 3.

Neurovasx, ePAX, http://www.neurovasx.com, accessed Jan. 2010, pp. 1.

Prosecution Document, Japanese Office Action dated Jun. 3, 2014 for Japanese Patent Application No. 2012-544799, pp. 1-5.

Small, IV, Ward et al., Biomedical applications of thermally activated shape memory polymers, J. Mater. Chem., Mar. 2, 2010, 20, Mar. 2, 2010, pp. 3356-3366.

University of California, Davis, Development of aneurysm treatment using laser-deployed shape memory polymer foams, http://cbst.ucdavis.edu/research/aneurysm-treatment/development-of-aneurysm-treatment-using-laser-deployed-shape-memory-polymer-foams, May 12, 2010, 3 pages.

Wilson, Thomas S. et al., Shape Memory Polymer Therapeutic Devices for Stroke, Smart Medical and Biomedical Senso Technology, III, Proc. of SPIE, vol. 6007 (2005), pp. 1-8.

Yakacki, Christopher J. et al., Optimizing the thermomechanics of shape-memory polymers for biomedical applications, Material Research Society Symposium Proceedings, vol. 855E, Dec. 1, 2004, pp. 106-111.

International Search Report for PCT/US2010/029742, dated Jan. 31, 2011; 4 pages.

\* cited by examiner

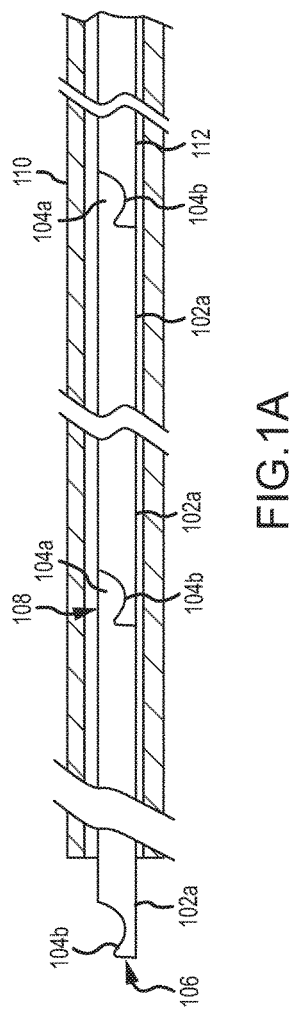
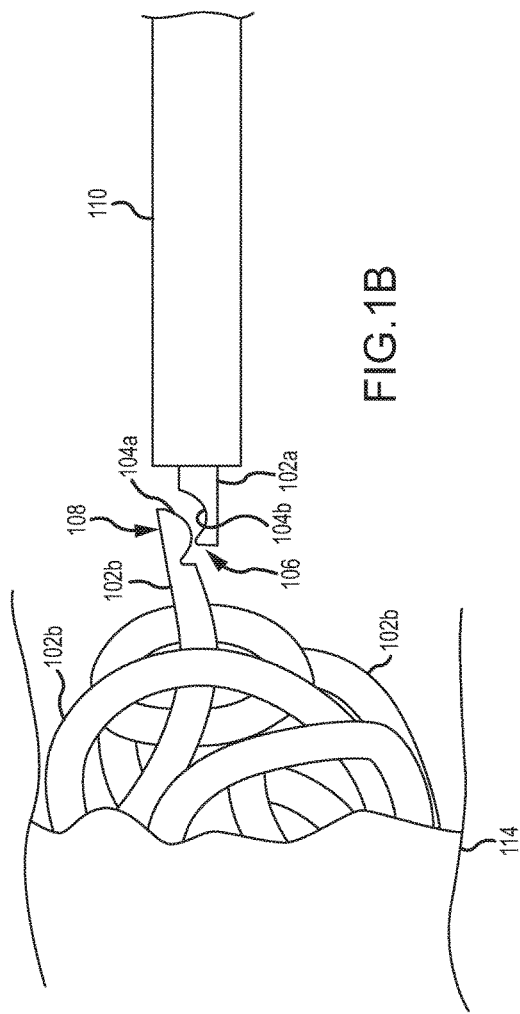
FIG.1A
FIG.1B

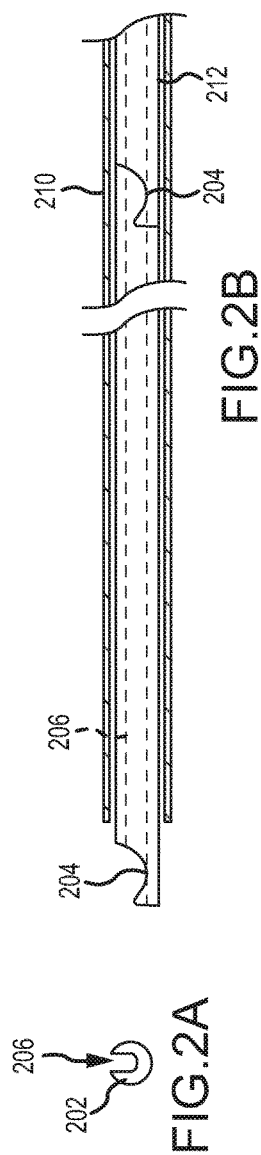

VASCULAR OCCLUSION DEVICES

CROSS REFERENCE TO RELATED APPLICATIONS

This application claims the benefit of priority pursuant to 35 U.S.C. §119(e) of U.S. provisional application No. 61/166,120 filed 2 Apr. 2009 entitled "Vascular occlusion devices," which is hereby incorporated herein by reference in its entirety for the purposes of PCT Rule 20.6.

The present application is also related to Patent Cooperation Treaty application no. PCT/US2006/060297 filed 27 Oct. 2006 entitled "A polymer formulation a method of determining a polymer and a method of determining a polymer fabrication," and Patent Cooperation Treaty application no. PCT/US2007/065691 filed 30 Mar. 2007 entitled "Shape memory polymer medical devices," which are hereby incorporated herein by reference in their entirety for the purposes of PCT Rule 20.6.

STATEMENT REGARDING FEDERALLY SPONSORED RESEARCH OR DEVELOPMENT

This technology was developed in part with sponsorship by National Science Foundation Grant Nos. 0823015 and 0848626 and the U.S. federal government has certain rights to this technology.

TECHNICAL FIELD

The technology described herein relates generally to implantable devices for interventional therapeutic treatment or vascular surgery, and more particularly concerns a endoluminally delivered device for vascular occlusion and or aneurysm repair.

BACKGROUND

Interventional radiology and interventional neuroradiology are medical disciplines expanding minimally invasive treatments for vascular defects and vascular malformations while avoiding the cost and burden of open surgery. Clinicians utilize various imaging modalities (primarily fluoroscopy) along with percutaneous (vascular access) guide and delivery catheters to routinely conduct vascular "stenting" to open or maintain patency of a diseased vessel lumen and vascular occlusion or embolization to stop the blood flow in a vessel or isolate a vascular area from blood flow.

Peripheral vascular (PV) intervention treatments include vascular occlusion for treating hemorrhages, aneurysms, and tumor isolation, including nephroma, hematoma, peripheral aneurysms, and other vascular malformations, and uterine fibroids among other conditions. Interventional neuroradiology (INR) treatments include treating cerebral vascular malformations such as arteriovenous malformations (AVMs) wherein the artery and vein are connected and a variety of cerebral aneurysms or bulging and weakening of a vessel wall. Vaso-occlusive (V-o) devices are used to isolate and/or fill the defect. Other INR procedures include occlusion of ateriovenous fistulae (AVF), parent vessel sacrifice (PVS), and tumor indications among other conditions.

The V-o devices can take a variety of configurations, and are generally formed of one or more members that are larger in the deployed configuration than when they are within the delivery catheter prior to placement. One widely used V-o device is a helical wire coil having a deployed configuration which may be dimensioned to engage the walls of the vessels. Some known anatomically shaped V-o devices form into a shape of an anatomical cavity such as an aneurysm and are made of a pre-formed strand of flexible, biocompatible material such as stainless steel, platinum, or a shape memory alloy, e.g., a nickel-titanium alloy (NiTinol). Such V-o devices comprise one or more members formed in a generally spherical or ovoid shape in a relaxed, or deployed state and the device is sized and shaped to fit within a vascular cavity or anomaly, such as for treatment of aneurysm or fistula. The V-o members are first formed in a generally linear fashion as a helical winding or braid. The generally linear V-o member is then configured and captured around an appropriately shaped mandrel or form and heat-treated so that the V-o members retain the complex shape in the relaxed or deployed state. The V-o device is then manipulated within its elastic deformation range into a less complex, generally straight, shape, i.e., its pre-deployed state, for insertion through a cannula and catheter. As such, the V-o member is a helical winding or braid on which a complex secondary shape is imposed.

Delivery of such a coil in the treatment of aneurysms or other types of arteriovenous malformations can be accomplished by a variety of means, including via a catheter in which a series of single coil devices is pushed through the catheter by a pusher to deploy the coil. The coils pass through the lumen of the catheter in a linear shape and take on a complex shapes as originally formed after being deployed into the area of interest, such as an aneurysm. A variety of detachment mechanisms to release the single coil from a pusher have been developed. To complete an occlusion procedure, the physician must sequentially reload the catheter with several individual coils until it is determined the occlusion is sufficient. This physician typically determines whether sufficient coils have been deployed by assessing the level of occlusion of the vessel flow or by evaluating the density of the coil packed into the aneurysm sack (i.e., the coil pack), both performed by typical medical imaging techniques. This "place and assess" method can extend the time and cost of the medical procedure and also can increase the imaging exposure (i.e., radiation exposure) to both the patient and the physician.

There are many known variations of metal embolic coils including those with offset helical and twisted shapes having multiple axially offset longitudinal or focal axes with a secondary shape having coiled ends and a middle loop. A stretch-resistant V-o coil is also known that is formed from a helically wound primary coil and a stretch resistant member, that can also have a secondary shape with coiled ends ad a middle loop, and an embolization coil having a single closed loop. Highly flexible coils with secondary shapes are also known that form occlusive implants that are sufficiently flexible that each can be folded upon itself and maintain that configuration. It has been found that single strands of small diameter nickel-titanium alloys, as well as other metal alloys, used to form metal V-o coils can be kinked if twisted and pulled as can occur during or after deployment from a catheter, especially if the doctor wishes to withdraw a partially deployed coil because it is somehow incorrect in size, shape, or length to effect the desired repair. Other coils utilize multiple strands of small diameter metal alloy wire to overcome this limitation. However, all of these methods of construction rely upon a costly metal alloy and significant processing costs to fabricate the embolic coil.

Wire wound coils can be further enhanced through coating and/or fiber attachment to induce specific tissue or thrombus response. However, the mechanical performance of these devices is limited by the single material properties of the base wire and the fabrication techniques associated with wire forming.

For larger vessel occlusion, metal wire coils present significant limitation and/or require a significant number of devices to achieve suitable vessel occlusion. Other, non-coil devices are known that may utilize an articulating mesh structure fabricated from similar metal alloys and wire-forming methods. While these devices can effectively occlude larger vessels, they are similarly very expensive and have proven to be challenging for the physician to place accurately due to the length of their pre-deployed state.

Traditional polymers that are not shape memory polymers cannot provide suitable "shape fixity" after storage in a stressed condition for extended periods. Traditional polymers suffer from "creep" resulting in a loss of shape fixity.

Polyester fibers and braiding have been added to the wire devices as a means to enhance thrombogenic response. Some coils are coated with a bioabsorbable polymer (PLGA, etc) as a means of enhancing blood/tissue interaction. Other coils are coated with a hydrogel to cause them to swell in-situ and provide a tighter coil pack. However, all of these products rely on an underlying metal coil design. Typically resilient materials such as shape memory metal alloys or superelastic metal alloys are used to maintain the unique coiled sample post deployment while the device is being held in a straight configuration inside of a coil holder (tube/hub device) that allows easy physician loading into the proximal end of the delivery catheter. Again, these devices suffer performance limitations and high cost constraints due to the underlying materials of construction.

The information included in this Background section of the specification, including any references cited herein and any description or discussion thereof, is included for technical reference purposes only and is not to be regarded subject matter by which the scope of the invention is to be bound.

SUMMARY

Various implementations of coil-shaped vascular occlusion (V-o) devices formed of shape memory polymer materials are disclosed. SMP material properties of the coil devices can be tailored, through formulation, for specific mechanical behavior and "clinician feel" of the coils. Concurrent coil diameter changes can enhance the relative change in stiffness along the length of the coil. SMP materials provide "shape fixity" properties, which enable unique configurations and shapes for storage and in-situ deployment, respectively. These two definitive shapes provide significant feature advantages over traditional elastomeric or flexible materials undergoing compression within the elastic range of such traditional materials.

In one implementation, multiple coil insertion capability is achieved via chaining coils within the coil introducer. The pre-deployment shape and configuration of a series of SMP coils allows for interconnection between coils and interconnection with a pusher to enable clinician control of the coil position and release from the catheter.

In another implementation, non-round cross sections in the SMP coil shape and configuration, as well as in the shape and configuration of the pusher, provide an effective channel that allows access for injection of imaging contrast agent or concurrent placement of small tools or instruments.

In an alternate embodiment, a single shape memory material occlusive device that transforms into multiple, smaller diameter coils in the deployed state may be used to generate a complex occlusive structure.

In a further implementation, a shape memory material occlusive device may be configured to deploy in an organized spring form. A fabric component may be attached to and extends along a length of the coil. The fabric may be collapsed or furled around the device in a pre-deployed state for storage and insertion in an introducer and catheter and then deploy with the spring-like coil in a deployed state. The fabric forms a single- or multiple-layer occlusive surface within a center of the spring-like coil resulting in an effective "vascular plug" from a single coil-type of device.

The SMP coils may contain other materials within the SMP matrix, included during formulation or during molding or extrusion processes that impart other beneficial properties. These materials may include, for example, radio-opacity, CT compatibility, bioactive agents, thrombogenic enhancing materials, fibers, or fabrics. The SMP coils may also be coated to provide beneficial characteristics, for example, reduction in friction from hydrophilic coatings. Smooth surface characteristics improve coil pack through reduction in friction between coil loops.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter. Other features, details, utilities, and advantages of the present invention will be apparent from the following more particular written description of various embodiments of the invention as further illustrated in the accompanying drawings and defined in the appended claims.

BRIEF DESCRIPTION OF THE DRAWINGS

FIG. 1A is a cross-section view of a catheter delivering a series of SMP coils connected in a chain and separable upon deployment from a distal end of the catheter.

FIG. 1B is side plan view of an occlusive mass of SMP coils deposited in a vessel from the distal end of a catheter after disengaging from the connective chain of pre-deployed coils in the catheter.

FIG. 2A is an end plan view of an SMP coil formed with a channel in a pre-deployment state.

FIG. 2B is a side plan view of the SMP coil of FIG. 2A formed with a channel in a pre-deployment state.

FIG. 2C is a cross-section view of the SMP coil of FIG. 2A formed with a channel inserted within a catheter.

DETAILED DESCRIPTION

Figure 3A:
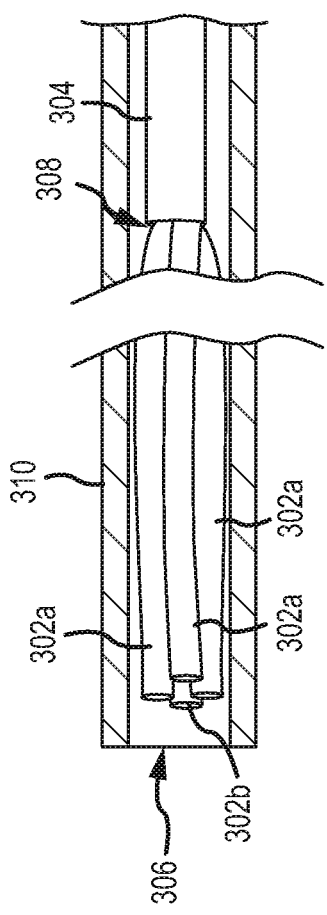
FIG. 3A is a cross-section view of a catheter delivering a shape memory coil device in a pre-deployed state formed with a collection of coil tendrils attached to a base.

As indicated, embolic coils come in a variety of shapes and sizes for specific purposes. Typically embolic coils are made from platinum and/or NiTinol metal wire, with and without exposed polyester fiber, which limits not only the clinical performance of such devices, but induces a high manufacturing cost.

In contrast, a shape memory polymer (SMP) formulation in an adapted molding or extrusion process significantly reduces the manufacturing cost while enabling unique cross-sectional shapes and forms unavailable using wire-forming fabrication techniques. Further, a shape memory polymer can be uniquely formulated to provide specific mechanical properties that result in superior occlusive performance through enhanced interaction between the coil, vessel tissue, and flow characteristics of the vessel or vascular malformation it is occluding. Meanwhile, the SMP occlusive coil is configured to be deployed using an existing delivery catheter using standard techniques.

Shape memory polymers demonstrate the phenomena of shape memory based on fabricating a segregated linear block co-polymer, typically of a cross-linked hard segment monomer and a soft segment monomer. The SMP generally is characterized by defining phases that result from glass transition temperature (Tg). Mechanical properties of the phases, i.e., the stored or pre-deployed shape (e.g., below the Tg) and the deployed shape (e.g., above the Tg), as well as setting the Tg, may be tailored by adjusting the formulation of the SMP through different weight percentages of the monomers and cross linker. (See Patent Cooperation Treaty application nos. PCT/US2006/060297 and PCT/US2007/065691.) Shape memory polymers can be formulated for a Tg that allows use of an external heat source to initiate the phase change or a Tg that utilizes the body heat of the patient to initiate the phase change.

The target vasculature for occlusion and/or vascular malformations (e.g., aneurysms, AVMs, etc.) are pathologic structures and present significant anatomical variability. The coil form and complex intertwining of coil loops provides a flexible and adaptive structure for achieving occlusion in these procedures. Coiling is well established in medical practice but generally utilizes coils manufactured from metals that will retain their unique coil shape after deployment subsequent to significant storage time being held in a straight coil introducer.

An SMP occlusive coil and its various configurations address key clinical needs that are currently unmet with existing metal coils. These may include the following:

Reduced procedure cost and time;

Better immediate occlusions (e.g., through better anchoring to the vasculature and better packing efficiency to block blood flow) which results in better clinical performance and clinical outcomes; and Capability for occluding larger diameter vessels from a small delivery catheter than currently achievable with existing coils.

The implementation of SMP materials in an occlusive coil or vascular plug also enables a device that generates much larger and more complex features while providing for deployment from a very small catheter.

SMP material mechanical properties may be tailored to achieve a preferred stiffness or softness for the coil. Further, the coil can be fabricated from SMPs of different formulations to create a multi-modulus material that results in varying stiffness along the length of the coil. This may, for example, allow the first few loops of a coil to be stiff for anchoring within the vascular tissue and the balance of the coil to be soft for improved packing efficiency and greater occlusion. Further, this material effect can be combined with diameter (dimensional) changes along the coil length to enhance the change in relative stiffness.

Competitive devices made from metal wire suffer from compromises so that their device is stiff enough to handle/insert and anchor on the vascular tissue and yet soft enough to fold and create a tightly packed occlusive mass. If the material is too stiff, it will not pack effectively allowing blood flow around the coil. If the material is too soft, it will not effectively anchor on the tissue wall and can migrate due to blood flow or manipulation of the sequential coil during the procedure. This compromise limits their design and undermines optimizing these conditions.

The SMP's "shape fixity" (representing two definitive and accurate shapes, those of pre- and post-thermal deployment/activation) provides the ability to accurately define and provide a straight insertion configuration that flexes and tracks down the long, small lumen of a delivery catheter placed in the body in a tortuous path to reach the target site, and separately define and provide a deployment configuration of a complex "secondary" coil shape that enables an efficient occlusive mass. These definitive shapes and features are enabled using a low cost fabricated SMP device in comparison to high cost shape memory alloys (SMA) such as NiTinol or in comparison to traditional polymers without shape memory. Traditional polymers without shape memory undergo continuous stress in a straight packaged configuration and could not survive the shelf life and packaging duration necessary and retain appropriate shape fixity post deployment.

As SMP materials are formulated for use, other ingredients can be added to the formulation to induce specific properties or behavior that may include, for example, radio-opacity, computed tomography (CT) compatibility, tissue response, thrombogenicity, or others, or any combination thereof. For example, barium methacrylate (in solution) or tungsten powder (in suspension), or a combination of these or similar ingredients may be added to the SMP material to induce radio-opacity. Fibers or fabric from materials such as polyester may be added and positioned for surface exposure to induce thrombogenicity. Bioactive agents (e.g., fibroblast growth factor) and eluting pharmaceuticals (e.g., NSAIDs such as ibuprofen) may be integrated in the matrix of the material. Further, the SMP material can be treated with coatings, for example, hydrophilic coatings to reduce friction or biodegradable coatings (e.g., polyglycolic acid) to induce a desired tissue response.

SMP materials using common molding and/or extrusion processing methods can result in very smooth and continuous coil surfaces. These surfaces can be beneficial for improving the effective coil pack in occlusion devices by reducing the friction between the coil loops. SMP materials can be combined in part with hydrogel materials to induce additional functionalities along the length of the coil, for example, preferred hydration-associated swelling at pre-set points along the length of the coil.

Interlocking Coil Configuration

In one implementation as shown in FIGS. 1A and 1B, occlusive vascular coils 102b may be formed in a pre-deployment state as elongate members 102a with the ability to chain elongate members 102a such that a coil introducer (i.e., the hub/tube holder that is used to insert the coil into the proximal end of a delivery catheter) can be filled with multiple, chained, sequential elongate members 102a. Interlocking the elongate members 102a in a serial chain allows greater control on position (e.g., push out, pull back) as needed. The chain connection is detachable such that, as the most distal elongate member 102a is pushed beyond the limit of the distal tip of the catheter 110, the engagement between successive interlocked elongate members 102a detaches and the deployed elongate member 102a is free to transform into a coil 102b. The chained elongate members 102a are further interlocked with a dedicated "pusher," a guidewire 112 that runs the length of the catheter 110 and which is connected at the proximal end of the chain of elongate members 102a. This pusher 112 may be used by the physician to advance (push) or retract (pull) the elongate members 102a from the proximal end of the catheter 110 outside the patient's body.

SMP elongate members 102a/coils 102b may be fabricated in specific lengths with end treatments that result in the interlocking connective features 104a/b. Elongate members 102a are linked together to support both push and pull actions. As shown in FIGS. 1A and 1B, the interlocking features 104a/b may be formed as complementary, hook-like features on opposite ends of each elongate member 102a for attachment with adjacent elongate members 102a. The functionality of the interlocking features 104a/b is dependent upon constraint of the elongate members 102a within the lumen of the catheter to delay deployment as coils 102b. Once the interconnection of the distal elongate member 102a is pushed beyond the distal end 106 of the catheter 110, the proximal end 108 of the distal elongate member 102a is no longer constrained and is free to separate from the distal end of the adjacent, proximal elongate member 102a in sequence remaining within the catheter 110. Sequential elongate members 102a are delivered this way to the target occlusive site until a desired number of coils 102b is placed within the vessel 114.

The chain of elongate members 102a is similarly connected to the dedicated pusher 112 in the control of the physician. If an elongate member 102a is only partially deployed, the proximal end is still connected and contained within the lumen of the catheter 110. If the physician dislikes the position or configuration of the distal end of the deploying elongate member 102a/coil 102b, he can pull the elongate member 102a/coil 102b back into the catheter 110 to reposition it before deploying and releasing the coil 120b. In this way, the elongate members 102a/coils 102b are applied in a push/pull motion. Because the coils 102b are fabricated from a very tough SMP material, they do not suffer permanent deformation of stretch or kinking that result from the push/pull motion and has been associated with thin metal alloy wire coils.

Channeled Coil Configuration

In other implementations as shown in FIGS. 2A-2C, SMP coils 202 may be fabricated with unique cross-sectional designs. While wire coils are round in shape, SMP coil forms are derived by extrusion die shapes or mold shapes. A contiguously connected channel 206 along the length of the elongated pre-deployment shape of the coils 202 can be formed cost-effectively through these processes. The cross-section of this SMP coil 202 in a pre-deployed shape may appear as a "C" or "U" in shape, or the pre-deployed coil 202 may be hollow. The open area channel 206 or lumen within and along the length of the pre-deployed coil 202, resident in the lumen of the catheter 210, may form a pathway or conduit for fluids, e.g., contrast media, or tools or instruments, e.g., a trimming device or micro-forceps. The shape of the channel 206 may be maintained through the interconnection structures 204 in chained pre-deployed coils 200 described above, providing continuity through the series of pre-deployed coils 202 within the catheter 210. The shape of the channel 206 is also accessible or maintained in the "pusher" wire 212 that the physician controls to advance or retract the coils 202.

The resulting channel path may be continuous from the distal end of the coil 202 in the catheter 210 within the patient to a Y-connector (not shown) that is connected to the proximal end of the catheter 210, outside the patient. The pusher 212 may enter the Y-connector from a straight port incorporating a sliding anti-backflow valve to allow injection of fluids from the side port on the Y-connector without leaking back and out the straight port. The Y-connector may incorporate a circumferential channel feature that eliminates the need to align the channel with the side port for fluid injection. However for tool access through the side port, the channel 206 may need to be rotated and aligned with the side port.

During typical coil deployment for occluding a flowing vessel, the physician may periodically inject contrast media for imaging enhancement to assess the quality of the coil pack. Typical prior art serial coils preclude the ability to inject contrast through a typical single lumen catheter after an individual coil is placed. In contrast, the present implementation provides, in both the chained coils and the detachable pusher, a cross-section for each of these elements that is defined such that a channel is formed that enables liquid contrast media to be injected from the proximal end (outside the patient) through the catheter holding the coils into the patient. This "puff while you place" configuration is unique to the molded/extruded aspects of the SMP coil as metal coils cannot be cost effectively formed with this channel. The channels line up through the assembly and communicate with the Y-connector at the proximal end to provide the path for the contrast media injected from a standard syringe.

Medusa Coil Configuration

Figure 3B:
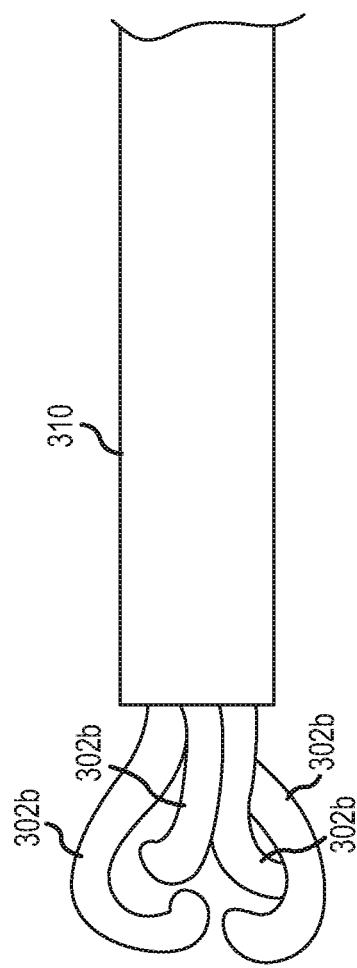
FIG. 3B is a side plan view of the coil device of FIG. 3A deploying from a catheter and forming a complex occlusive coil structure.

In another implementation, a unique shape memory material occlusive coil configuration is depicted in FIGS. 3A and 3B. Within a given diameter of the delivery catheter 310, multiple (smaller diameter) coils 302b may be configured adjacent to each other resulting in a pre-deployed elongate shape 302a sized to fit within the single lumen catheter 310. The multiple elongate members 302a/coils 302b may be joined at a plug 304 the proximal end 308 or alternatively, also at the distal end 306 (not shown). These multiple coils 302b are not sequential but parallel in delivery. Upon deployment, the multiple coils 302b are expressed from the catheter 310 changing shape and generating a much more complex coil mass that could be achieved by expressing a single coil. This multi-coil approach provides the ability to occlude larger vessels and/or generate an effective occlusive mass quickly.

Note that this configuration is not the same as a multiple-strand wire coil. In the latter, the multiple strands are gathered together to form a single member that deploys into a single coil shape. This shape memory material coil implementation utilizes multiple, separate coils 302b connected together at plug 304 at one end to deploy simultaneously. This facilitates quickly achieving an occlusive mass for larger vessels with one device. In this implementation, the shape memory material may be an SMP as described herein, a shape memory metal alloy, or other shape memory material.

Vascular Plug

In yet another implementation depicted in FIGS. 4A-4D, SMP coil vascular plugs 400 may be utilized for larger diameter vessels in which coil nests are not very effective or results in a massive number of coils used to achieve the occlusion. Existing metal vascular plug devices present other challenges by requiring larger catheters for delivery and imposing longer rigid portions of the device, ultimately making it more difficult to reach and precisely locate its deployed position. Delivering a shape memory material vascular plug using a coiling technique provides many advantages in addressing these issues. A shape memory vascular plug 400 allows significantly larger deployed coil-shape (i.e., a large diameter) from a small delivery catheter 410. In this implementation, the shape memory coil 402b does not form an occlusive mass of coil loops. Instead, the vascular plug 400 organizes, like a coil spring 402b, against the wall of the vessel 414. In this implementation, the shape memory material may be an SMP as described herein, a shape memory metal alloy, or other shape memory material.

Figure 4A:
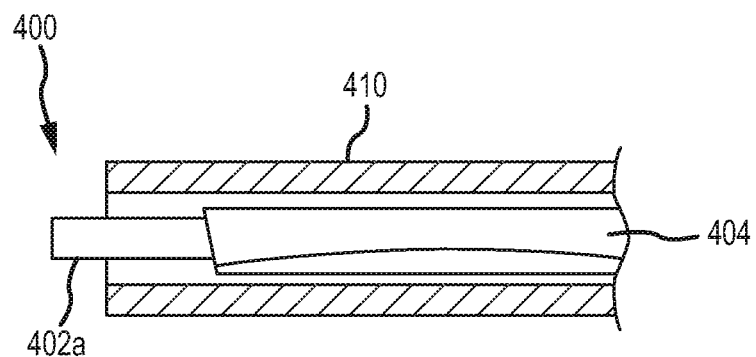
FIG. 4A is a cross-section view of a catheter delivering a shape memory occlusive device in a pre-deployed state formed with a fabric component attached to and furled around a sidewall of the device.
Figure 4B:
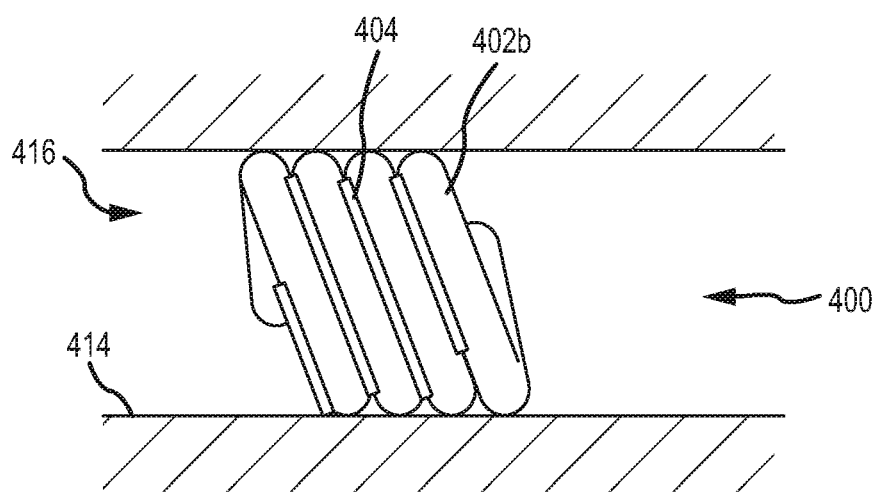
FIG. 4B is a side plan view of the device of FIG. 4A deployed within a vessel and forming a spring-shape coil with the fabric unfurled within the center of the coil.
Figure 4C:
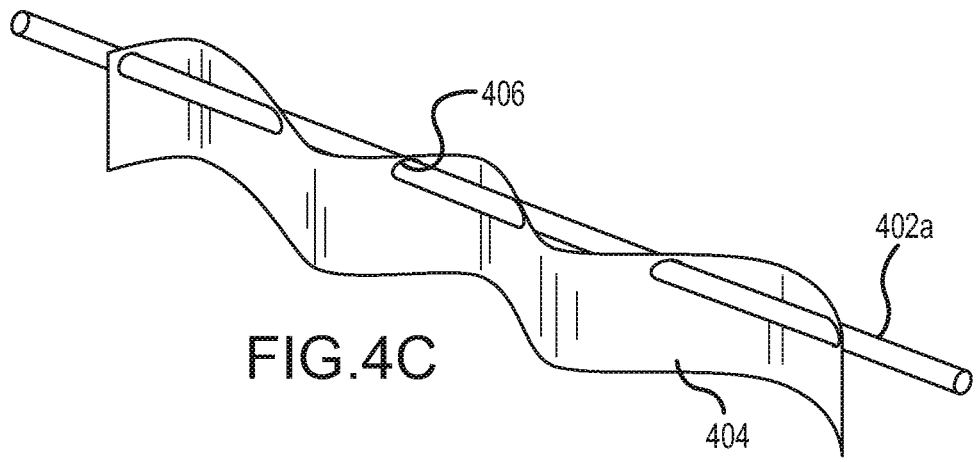
FIG. 4C is an isometric view of the device of FIG. 4A in a pre-deployed state with the fabric component threaded along the length of the device.

Inherent in the coil plug 400 is a section of fabric 404 (e.g., a biocompatible polyester fabric) attached to and rolled along a length of the elongated member 402a when straightened for introduction through the catheter 410. The fabric 404 has a specific configuration and attachment to the elongated member 402a/coil 402b. In one implementation, the fabric 404 defines multiple holes 406 along an edge, like a shower curtain. The vascular occlusion device 400 in its pre-deployed state is passed through the holes 406 of the fabric 404. The fabric 404 is free to slide along the elongate member 402a as shown in FIG. 4C. The fabric 404 is then rolled up around the straight elongate member 402 and the device 400 is placed in the catheter 410 as shown in FIG. 4A. Upon deployment from the catheter 410, as the coil spring 402b forms from the pre-deployment elongate shape, the fabric 404 unfurls and positions itself across the vessel lumen 416 as shown in FIG. 4B resulting in physical blockage of the lumen 416. The length of the fabric 404 is such that as the coil spring form takes shape, the fabric 404 presents redundant layers across the lumen 416 to form the effective vascular plug 400 as shown to good advantage in FIG. 4D.

Figure 4D:
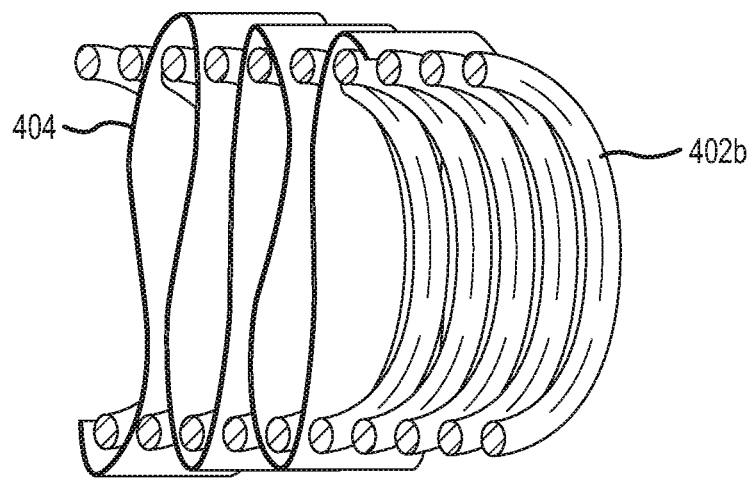
FIG. 4D is an isometric view in cross section of the device of FIG. 4B deployed within a vessel and forming a spring-shape coil with the fabric unfurled within the center of the coil.
Figure 5:
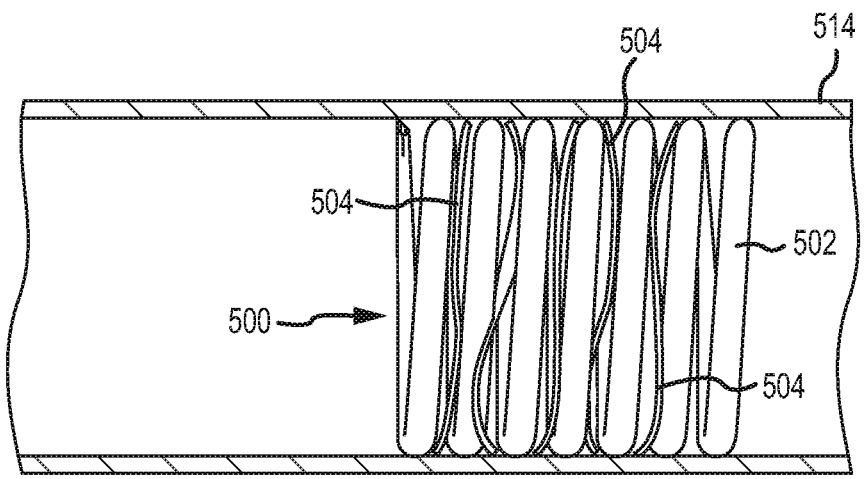
FIG. 5 is a side elevation view in partial cross section of an alternate implementation of a vascular occlusive device deployed within a vessel and forming a spring-shape coil with a series of fabric panels attached at points along the coil to hang within the center of the coil.

In an alternate implementation of a vascular occlusive device 500 as shown in FIG. 5, the device 500 is deployed within a vessel 514 and forms a spring-shape coil 502 as in FIG. 4D. However, in this embodiment a series of fabric panels 504 are attached at points along the coil 502 to hang between turns of the coil 502 within the center of the coil 502. The fabric panels 504 may be adhered to the surface of the coil 502, partially embedded in the material of the coil 502 during manufacturing, or attached by other methods. Again, in this implementation, the shape memory material may be an SMP as described herein, a shape memory metal alloy, or other shape memory material.

In each of these implementations, the coil thus acts as an anchor along the vessel wall and the fiber/fabric forms an occlusive barrier to blood flow within the lumen. The fabric is designed and cut to a specific shape and flexibility to enable proper deployment. The fabric may be attached at strategic points along the coil to facilitate packaging wherein the fabric is rolled around the coil or otherwise condensed in size such that both the coil and the fabric fit within the diameter of the coil introducer and associated catheter. The straightened coil with fabric is deployed by advancing it down the catheter, using a typical pusher, and pushing it out the distal end at the target occlusion site. As the coil deploys and regains its memorized shape, the coil expands radially and pushes against the vessel wall to develop the anchor function while achieving a round, generally spring-like shape. The fabric unrolls/unfurls and is biased to be positioned within the center of the lumen. Sections of the fabric may overlap with each turn of the coil spring such that a redundant flow barrier is achieved upon complete deployment.

All directional references (e.g., proximal, distal, upper, lower, upward, downward, left, right, lateral, front, back, top, bottom, above, below, vertical, horizontal, clockwise, and counterclockwise) are only used for identification purposes to aid the reader's understanding of the present invention, and do not create limitations, particularly as to the position, orientation, or use of the invention. Connection references (e.g., attached, coupled, connected, and joined) are to be construed broadly and may include intermediate members between a collection of elements and relative movement between elements unless otherwise indicated. As such, connection references do not necessarily infer that two elements are directly connected and in fixed relation to each other. The exemplary drawings are for purposes of illustration only and the dimensions, positions, order and relative sizes reflected in the drawings attached hereto may vary.

The above specification, examples and data provide a complete description of the structure and use of exemplary embodiments of the invention. Although various embodiments of the invention have been described above with a certain degree of particularity, or with reference to one or more individual embodiments, those skilled in the art could make numerous alterations to the disclosed embodiments without departing from the spirit or scope of this invention. In particular, it should be understood that the described technology may be employed independent of a personal computer. Other embodiments are therefore contemplated. It is intended that all matter contained in the above description and shown in the accompanying drawings shall be interpreted as illustrative only of particular embodiments and not limiting. Changes in detail or structure may be made without departing from the basic elements of the invention as defined in the following claims.

What is claimed is:

1. An occlusive vascular device comprising
   a molded or extruded shape memory polymer material that is formed
   in a pre-deployed state as a monolithic, non-wound elongate member configured for delivery via a catheter and having
      a first interlocking structure formed of the same shape memory polymer material as part of the elongate member on a distal end thereof; and
      a second interlocking structure formed of the same shape memory polymer material as part of the elongate member on a proximal end thereof and configured to engage with an interlocking structure on another of the occlusive vascular device of a same shape as the first interlocking structure to form a gapless joint to enable linking of two of the elongate members together in succession; and
   in a deployed state as a coiled member, which coils from a form of the elongate member.

2. The occlusive vascular device of claim 1, wherein a diameter of the occlusive vascular coil varies along a length of the coiled member in the deployed state.

3. The occlusive vascular device of claim 1, wherein the shape memory polymer material comprises multiple formulations within the occlusive vascular coil and a modulus of the shape memory polymer material varies along a length of the coiled member in the deployed state.

4. The occlusive vascular device of claim 1, wherein the shape memory polymer material comprises one or more of the following additional materials: a radio-opacity material, a computed tomography (CT) compatible material, a tissue response material, a medication, or a thrombogenicity agent or material.

5. The occlusive vascular device of claim 1, wherein the shape memory polymer material is coated with one of more of the following additional materials: a hydrophilic coating, a thrombogenic coating, or a biodegradable coating.

6. The occlusive vascular device of claim 1, further comprising a fluid channel extending from the proximal end to the distal end of the elongate member through an entire length of the elongate member including through the first and second interlocking structures, wherein the fluid channel is C-shaped, U-shaped or formed as a rounded lumen within the elongate member.

7. A collection of occlusive vascular devices comprising a first occlusive device comprising
   a molded or extruded shape memory polymer material that is formed
   in a pre-deployed state as a monolithic, non-wound, elongate member configured for delivery via a catheter, wherein a fluid channel is formed along an entire length of the elongate member from a distal end to a proximal end to provide a continuous fluid channel through the elongate member; and
   in a deployed state as a coiled member, which coils from a form of the elongate member, wherein
   the fluid channel is defined by at least two continuous opposing side walls and a continuous base wall formed between the opposing side walls, each of the base wall and side walls extending entirely through the elongate member from the proximal end to the distal end; and
   at least a second occlusive device identical to the first occlusive device; wherein
   the collection includes at least both the first and second occlusive devices which, when connected end to end in series, provide a continuous fluid channel configured to transmit fluid through each elongate member from the proximal end of a most proximal of the first and second occlusive devices to the distal end of a most distal of the first and second occlusive devices.

8. The occlusive vascular device of claim 7, wherein the channel is C-shaped, U-shaped or formed as a rounded lumen within the elongate member.

9. The occlusive vascular device of claim 7, wherein the shape memory polymer material comprises one of more of the following additional materials: a radio-opacity material, a computed tomography (CT) compatible material, a tissue response material, a medication, or a thrombogenicity agent or material.

10. The occlusive vascular device of claim 7, wherein the shape memory polymer material is coated with one of more of the following additional materials: a hydrophilic coating, a thrombogenic coating, or a biodegradable coating.

11. The occlusive vascular device of claim 7, wherein the elongate member further comprises a first interlocking structure on a distal end thereof and a second interlocking structure on a proximal end thereof configured to engage with the first interlocking structure on another of the occlusive vascular device.

12. The occlusive vascular device of claim 7, wherein a diameter of the coiled member varies along a length of the coiled member in the deployed state.

13. An occlusive vascular device comprising
   a shape memory material that is formed
   in a pre-deployed state as a elongate member;
   in a deployed state as a spring-shaped coil configured to anchor against a vascular lumen; and
   a fabric attached to and extending along a length of the occlusive vascular device, wherein
   the fabric is collapsed about the elongate member in the pre-deployed state; and
   the fabric is unfurled to span across and extend interstitially between successive windings of the spring-shaped coil and occlude the vascular.

14. The occlusive vascular device of claim 13, wherein the shape memory material is a shape memory polymer.

15. The occlusive vascular device of claim 13, wherein the shape memory material is a shape memory metal alloy.

* * * * *